(12) United States Patent
Caillieux (10) Patent No.: US 11,129,946 B2
(45) Date of Patent: Sep. 28, 2021

(54) GUIDING DEVICE FOR DENTAL ANESTHESIA

(71) Applicant: Nicholas Caillieux, Troyes (FR)

(72) Inventor: Nicholas Caillieux, Troyes (FR)

( * ) Notice: Subject to any disclaimer, the term of this patent is extended or adjusted under 35 U.S.C. 154(b) by 698 days.

(21) Appl. No.: 15/121,850

(22) PCT Filed: Feb. 27, 2015

(86) PCT No.: PCT/IB2015/000699
§ 371 (c)(1),
(2) Date: Aug. 26, 2016

(87) PCT Pub. No.: WO2015/128736
PCT Pub. Date: Sep. 3, 2015

(65) Prior Publication Data
US 2017/0028143 A1    Feb. 2, 2017

Related U.S. Application Data

(60) Provisional application No. 61/945,499, filed on Feb. 27, 2014.

(51) Int. Cl.
*A61M 5/46* (2006.01)
*A61M 5/32* (2006.01)
(Continued)

(52) U.S. Cl.
CPC ........... *A61M 5/46* (2013.01); *A61M 5/3287* (2013.01); *A61M 19/00* (2013.01);
(Continued)

(58) Field of Classification Search
CPC .......... A61M 5/3287; A61M 5/42–427; A61M 5/46; A61M 25/0662; A61M 2210/0625;
(Continued)

(56) References Cited

U.S. PATENT DOCUMENTS

2006/0106342 A1* 5/2006 Cox ..................... A61M 5/3287
604/110

FOREIGN PATENT DOCUMENTS

EP        2429618 B1 *  2/2017  ............. A61C 19/00
FR        2 585 542        2/2005
(Continued)

OTHER PUBLICATIONS

Machine Translation of EP 2 429 618 B1 Obtained from Google Translate on Jul. 1, 2020. (Year: 2020).*

*Primary Examiner* — Theodore J Stigell
*Assistant Examiner* — Larry R. Wilson
(74) *Attorney, Agent, or Firm* — Cozen O'Connor (57) ABSTRACT

The invention provides a device for the practice of oral medicine, including dentistry. Specifically, the invention relates to a guiding device that helps to prevent injecting beyond the pterygomandibular space during inferior alveolar nerve block for which purpose the injection is administered in the vicinity of the inferior alveolar nerve. The device has a retro-mandibular tip (12) operably linked to a guide tube (14) by a connecting unit (20, 22, 24), the guide tube (14) is adapted to receive a syringe and has a stopper mechanism (19) to stop the advancement of the syringe such that its needle is located at a predetermined distance from the posterior edge of the mandibular ramus.

18 Claims, 9 Drawing Sheets

(51) Int. Cl.
*A61M 19/00* (2006.01)
*A61M 25/06* (2006.01)
*A61C 1/08* (2006.01)

(52) U.S. Cl.
CPC ........... *A61M 25/0662* (2013.01); *A61C 1/08* (2013.01); *A61M 2210/0631* (2013.01)

(58) Field of Classification Search
CPC .. A61M 2210/0631; A61M 2210/0637; A61B 17/176; A61C 19/00; A61C 19/063; A61C 19/08; A61C 1/08; A61C 1/082; A61C 1/084; A61C 1/087
See application file for complete search history.

(56) References Cited

FOREIGN PATENT DOCUMENTS

| | | | |
|---|---|---|---|
| FR | 2 858 542 | 2/2005 | |
| WO | WO 2010/097520 | 9/2010 | |
| WO | WO 2012/139155 | 10/2012 | |
| WO | WO-2012139155 A1 * | 10/2012 | ............. A61C 19/00 |

* cited by examiner

GUIDING DEVICE FOR DENTAL ANESTHESIA

PRIORITY CLAIM

This is a U.S. national stage of application No. PCT/IB/2015/000699, filed on Feb. 27, 2015. Priority is claimed on U.S. Provisional Application No. 61/945,499, filed Feb. 27, 2014, the content of which is incorporated here by reference.

FIELD OF THE INVENTION

The invention relates to a device for the practice of oral medicine, including dentistry. Particularly, the invention relates to a guiding device for administering an injection of anesthesia in the vicinity of an inferior alveolar nerve. More particularly, the invention relates to a guiding device that helps to prevent injecting beyond the pterygomandibular space during inferior alveolar nerve block.

BACKGROUND OF THE INVENTION

The inferior alveolar nerve is unusual in having a passage inside the mandibular bone, protected by a cortical layer. Inferior alveolar nerve block (IANB) is the preferred anesthetic technique for dental and oral surgery procedures, involving the infiltration of the nerve before its entry into the mandibular canal.

In spite of certain complications and a failure rate varying from 5 to 20%, IANB remains the technique most frequently used for dental or oral surgery procedures involving the mandible. To be effective, the projection point of the needle must be in contact with the medial surface of the mandibular ramus, above and posterior to the lingula of the mandible. To achieve this, some authors have described intra-oral landmarks, which may vary depending on individual morphology. According to the anatomical technique in the art, the body of the syringe is oriented toward the contralateral molars or premolars, depending on the orientation of the mandibular ramus. The needle penetration point is at the center of an inverted mucosal triangle formed by the projection of the anterior edge of the mandibular ramus (outside), the medial pterygoid muscle (inside), and the bottom of the vestibule (above).

Numerous techniques exist for analgesia of the inferior alveolar nerve in a limited area of the pterygomandibular space, which reflects the difficulties encountered by practitioners.

For guide devices used in existing syringe analgesia mandibular foramen (EP 2009/2429618), the locking of the syringe and the injection are when the tip of the needle comes into abutment against the medial side of the ramus (i.e., at the bone contact). However, upon its penetration into the soft tissue, the needle may bend, deflect, or slide along the pterygomandibular fascia thereby changing the trajectory imposed by the device. The tip can then be found beyond the pterygomandibular space (in parotid space). An injection into the parotid space may result in a temporary paralysis of the facial nerve.

Accordingly, there exists a need for a guiding device that does not inject beyond the pterygomandibular space during inferior alveolar nerve block.

SUMMARY OF THE INVENTION

In one embodiment, the invention relates to a guiding device for administering an injection of anesthesia in the vicinity of an inferior alveolar nerve, in a subject, the device comprising: a retro-mandibular tip operably linked to a guide unit, said guide unit adapted to receive a syringe, wherein said guide unit comprises a mechanism adapted to hold said syringe such that its needle is located at a predetermined distance from the posterior edge of the mandibular ramus.

In another embodiment, the invention relates to a guiding device for administering an injection of anesthesia in the vicinity of an inferior alveolar nerve, in a subject, the device comprising: a retro-mandibular tip operably linked to a guide tube, said guide tube adapted to receive a syringe, wherein said guide tube comprises a stopper mechanism adapted to stop the advancement of said syringe, passing through said guide tube, at a predetermined point in said syringe. In a particular embodiment, the stopper mechanism is adapted to stop the advancement of said syringe when its needle is located at a distance, ranging between about 7 mm and about 25 mm, from the posterior edge of the mandibular ramus.

In another embodiment, the invention relates to a method of administering an injection of anesthesia in the vicinity of an inferior alveolar nerve of a subject, the method comprising the steps of: a) providing a guiding device, the device comprising a retro-mandibular tip operably linked to a guide unit, said guide unit adapted to receive a syringe, wherein said guide unit comprises a mechanism adapted to hold said syringe such that its needle is located at a distance, ranging between about 7 mm and about 25 mm, from the posterior edge of the mandibular ramus; b) holding said device in place in contact with a facial region relating to a mandible; c) inserting a syringe through said guide tube of said device; and d) administering the injectable medium at a location immediately before the inferior alveolar enters the mandibular foramen.

In another embodiment, the invention relates to a method of administering an injection of anesthesia in the vicinity of an inferior alveolar nerve of a subject, the method comprising the steps of: a) providing a guiding device, the device comprising a retro-mandibular tip operably linked to a guide tube, said guide tube adapted to receive a syringe, wherein said guide tube comprises a stopper mechanism adapted to stop the advancement of said syringe, passing through said guide tube, at a predetermined point in said syringe; b) holding said device in place in contact with a facial region relating to a mandible; c) inserting a syringe through said guide tube of said device; and d) administering the injectable medium at a location immediately before the inferior alveolar enters the mandibular foramen.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

The invention provides a guiding device for administering an injection of anesthesia in the vicinity of an inferior alveolar nerve. Specifically, the invention provides a guiding device that helps to prevent injecting beyond the pterygomandibular space during inferior alveolar nerve block.

In one embodiment, provided herein is a guiding device for administering an injection of anesthesia in the vicinity of an inferior alveolar nerve, in a subject, the device comprising: a retro-mandibular tip operably linked to a guide unit, said guide unit adapted to receive a syringe, wherein said guide unit comprises a mechanism adapted to hold said syringe such that its needle is located at a predetermined distance from the posterior edge of the mandibular ramus.

In another embodiment, provided herein is a guiding device for administering an injection of anesthesia in the vicinity of an inferior alveolar nerve, in a subject, the device comprising: a retro-mandibular tip operably linked to a guide tube, said guide tube adapted to receive a syringe, wherein said guide tube comprises a stopper mechanism adapted to stop the advancement of said syringe, passing through said guide tube, at a predetermined point in said syringe.

In another embodiment, provided herein is a method of administering an injection of anesthesia in the vicinity of an inferior alveolar nerve of a subject, the method comprising the steps of: a) providing a guiding device, the device comprising a retro-mandibular tip operably linked to a guide unit, said guide unit adapted to receive a syringe, wherein said guide unit comprises a mechanism adapted to hold said syringe such that its needle is located at a predetermined distance from the posterior edge of the mandibular ramus; b) holding said device in place in contact with a facial region relating to a mandible; c) inserting a syringe through said guide tube; and d) administering the injectable medium at a location immediately before the inferior alveolar enters the mandibular foramen.

In another embodiment, provided herein is a method of administering an injection of anesthesia in the vicinity of an inferior alveolar nerve of a subject, the method comprising the steps of: a) providing a guiding device, the device comprising a retro-mandibular tip operably linked to a guide tube, said guide tube adapted to receive a syringe, wherein said guide tube comprises a stopper mechanism adapted to stop the advancement of said syringe, passing through said guide tube, at a predetermined point in said syringe; b) holding said device in place in contact with a facial region relating to a mandible; c) inserting a syringe through said guide tube; and d) administering the injectable medium at a location immediately before the inferior alveolar enters the mandibular foramen.

Human mandible and inferior alveolar nerve block are fully described in U.S. Pat. Nos. 6,139,529 and 8,257,341; U.S. Patent Application Publication 201 10236866; and PCT International Patent Application Publication WO2010/097520, all of which are incorporated herein in their entirety.

Figure 1:
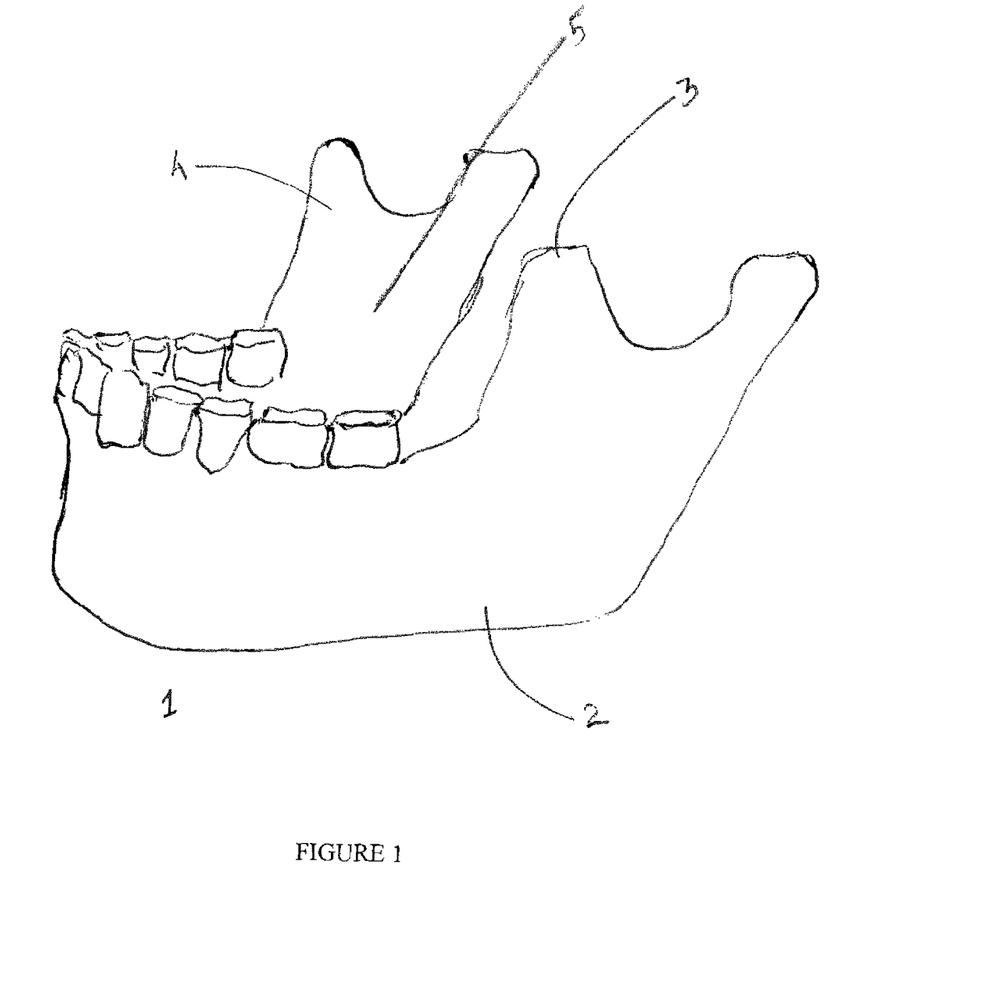
FIG. 1 is an example of an illustration of a mandible of a human.

FIG. 1 shows a human mandible 1, which is a lower jaw. Mandible 1 includes ramus 2, which is quadrilateral in shape and has two surfaces, a lateral flat surface and a medial surface 4. The medial surface 4 presents about its center the mandibular foramen 5, for the entrance of the inferior alveolar vessels and nerve. The medial pterygoid (or internal pterygoid muscle), is a thick, quadrilateral muscle of mastication. Its fibers pass downward, lateral, and posterior, and are inserted, by a strong tendinous lamina, into the lower and back part of the medial surface 4 of the ramus 2 and angle of the mandible 1, as high as the mandibular foramen 5.

Mandibular foramen 5 on the internal surface of ramus 2 provides an ideal location for administering anesthesia to a patient. Generally, the anesthesia is administered near the mandible foramen 5 to cause blockage of the nerve and the nearby lingual nerve for subsequent dental procedures.

However, this process has proven difficult because of the existence of soft tissue as well as small space to work, combined with various anatomical variations. As discussed above, for guide devices used in existing syringe, the tip of the needle comes into abutment against the medial side of the ramus 2. Upon its penetration into the soft tissue, the needle may bend, deflect, or slide along the pterygomandibular fascia thereby changing the trajectory imposed by the device. The tip can then be found beyond the pterygomandibular space (in parotid space), resulting in a temporary paralysis of the facial nerve.

The inventor of the instant patent application developed a device that overcomes the aforementioned problems. Specifically, the inventor of the instant application developed a guiding device that helps to prevent injecting beyond the pterygomandibular space during inferior alveolar nerve block.

Figure 2:
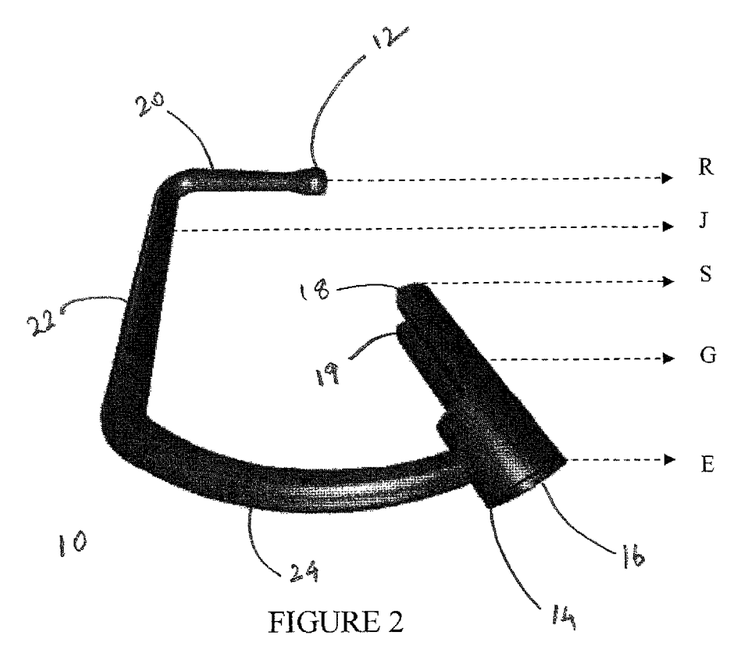
FIG. 2 shows a guiding device, according to one embodiment of the invention.

As shown in FIG. 2, guiding device 10 includes a retro-mandibular tip 12 and a guide tube 14. Retro-mandibular tip 12 helps a user (e.g., dental practitioner) to position the device 10 in place in contact with a facial region relating to mandible 1. Retro-mandibular tip 12 can be any suitable shape or size.

Figure 3A:
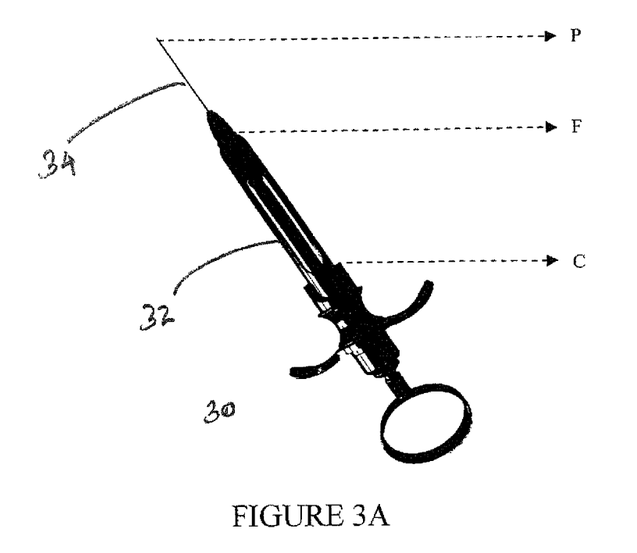
FIG. 3A shows a syringe for administering a dental anesthetic medicament, according to another embodiment of the invention.
Figure 3B:
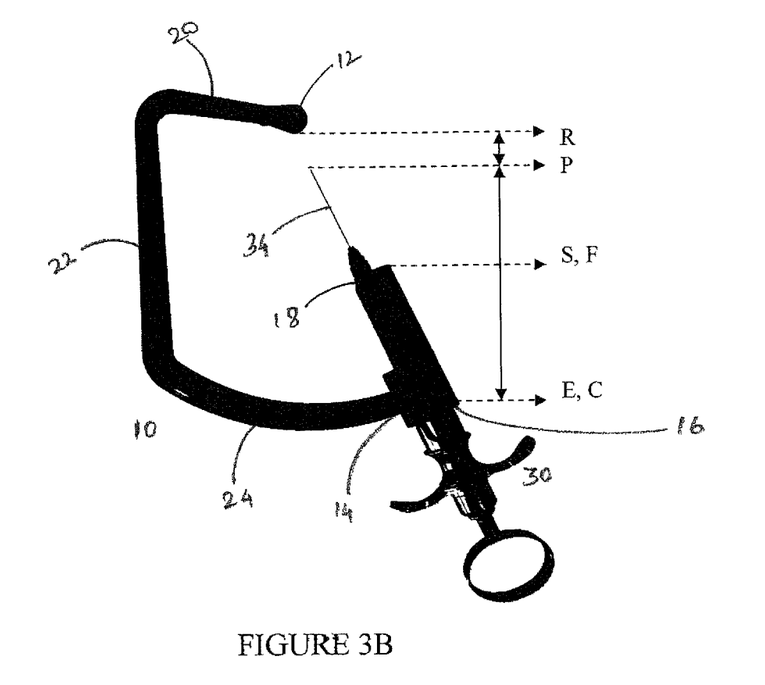
FIG. 3B shows a guiding device having a syringe, according to another embodiment of the invention.

Guide tube 14 is adapted to receive and hold a syringe 30, as shown in FIG. 3B. The invention is not limited to a tube shaped unit. Any guide unit capable of receiving and holding syringe 30 can be used. In one aspect, guide tube 14 includes inlet port 16 and outlet port 18. Syringe 30 can pass or advance through guide tube 14. Inlet port 16 provides as an entry point for syringe 30. After its entrance, syringe 30 can pass or advance through the body of guide tube 14. In one example, one or more portions of syringe 30 (e.g., needle 34) can pass through outlet port 18.

In a particular embodiment, guide tube 14 includes mechanism adapted to hold syringe 30 such that, during dental anesthesia, its needle 34 is located at a predetermined distance, for example, ranging between about 7 mm and about 25 mm, from the posterior edge of the mandibular ramus 2. In one example, the mechanism is a stopper mechanism 19 adapted to stop the advancement of said syringe 30, passing through said guide tube 14, at a predetermined point in syringe 30. In some embodiments, outlet port 18 has a reduced diameter relative to the diameter of inlet port 16 such that the guide tube 14 abuts against the end of the syringe body 32.

Any stop or lock mechanism, known to one of skilled in the art, capable of stopping the advancement of syringe 30 passing through said guide tube 14 can be used. Examples of such mechanisms, include, but are not limited to hinge and knob.

Stopper mechanism 19 holds syringe 30 or stops advancement of syringe 30 at a predetermined point such that its needle 34 is located at a predetermined distance from the posterior edge of the mandibular ramus 2. The predetermined distance may range between about 7 mm and about 25 mm, preferably 15 mm. In a particular embodiment, the predetermined distance is about 15 mm. In some embodiments, the predetermined distance may range between about 7 mm and about 15 mm, and preferably between about 9 mm and 12 mm.

Retro-mandibular tip 12 is operably linked to guide tube 14 by any suitable connecting mechanisms known to one of skilled in the art. In some embodiments, connecting mechanism includes one or more connecting arms (e.g., items 20, 22, and 24 shown in FIG. 2). Connecting arms can be linear (e.g., 20 and 22) or angled (e.g., 24) as long as the orientation of guide tube 14 and retro-mandibular tip 12 are positioned such that the guiding axis of the device 10 projects against medial surface 4 of the mandibular ramus 2 no more than the predetermined distance, discussed herein, from the posterior edge of the mandibular ramus 2.

Figure 4:
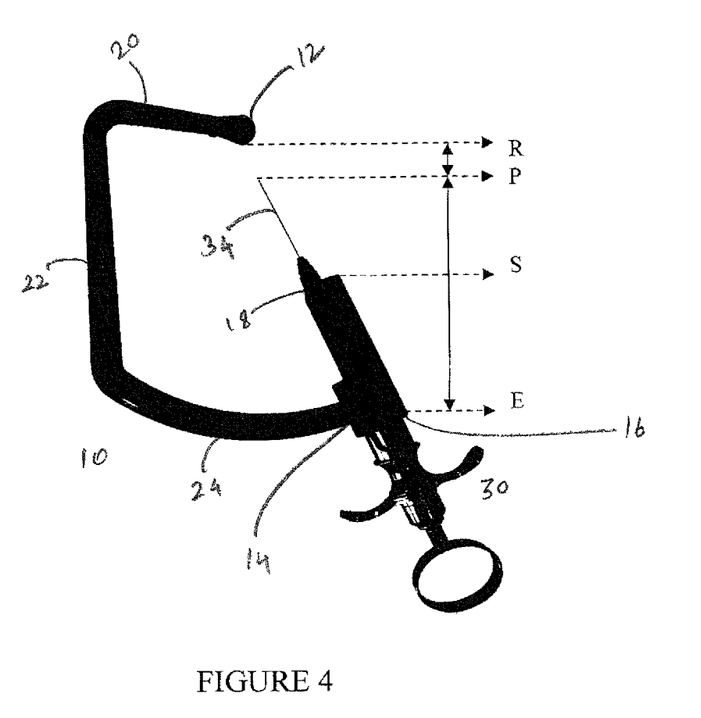
FIG. 4 shows a guiding device having a syringe, according to another embodiment of the invention.

In some embodiments, as shown in FIGS. 3B and 4, the stopper mechanism 19 is adapted to stop advancement of syringe 30 such that the distance between the edge of the inlet port 16 and the retro-mandibular tip 12 edge (ER) equals the sum of the distance between the edge of the inlet port 16 and the point of needle 34 (EP) and the distance between and the point of needle 34 and the retro-mandibular tip 12 edge (PR).

In one embodiment, as shown in FIGS. 3B and 4, the stopper mechanism 19 is adapted to stop advancement of syringe 30, in accordance with the following relationship:

$ER=EP+PR$, wherein ER refers to the distance between the edge of the inlet port 16 and the retro-mandibular tip 12 edge, EP refers to the distance between the edge of the inlet port 16 and the point of needle 34, and PR refers to the distance between the point of needle 34 and the retro-mandibular tip 12 edge.

As shown in FIG. 3B, the position of said guide tube also reflects the length of the needle 34 (PF) and the length of a portion of the syringe 30 body (FC).

In some embodiments, as shown in FIG. 3B, the stopper mechanism 19 is adapted to stop advancement of syringe 30 such that the distance between the edge of the outlet port 18 and the retro-mandibular tip 12 edge (SR) equals the sum of the needle 34 length (PF) and the distance between the point of needle 34 and the retro-mandibular tip 12 edge (PR).

In one embodiment, as shown in FIG. 3B, the stopper mechanism 19 is adapted to stop advancement of syringe 30, in accordance with the following relationship:

$SR=PF+PR$, wherein SR refers to the distance between the edge of the outlet port 18 and the retro-mandibular tip 12 edge, PF refers to the needle 34 length, and PR refers to the distance between and the point of needle 34 and the retro-mandibular tip 12 edge, and wherein said PR ranges, for example, from about 7 mm to about 25 mm.

Figure 5:
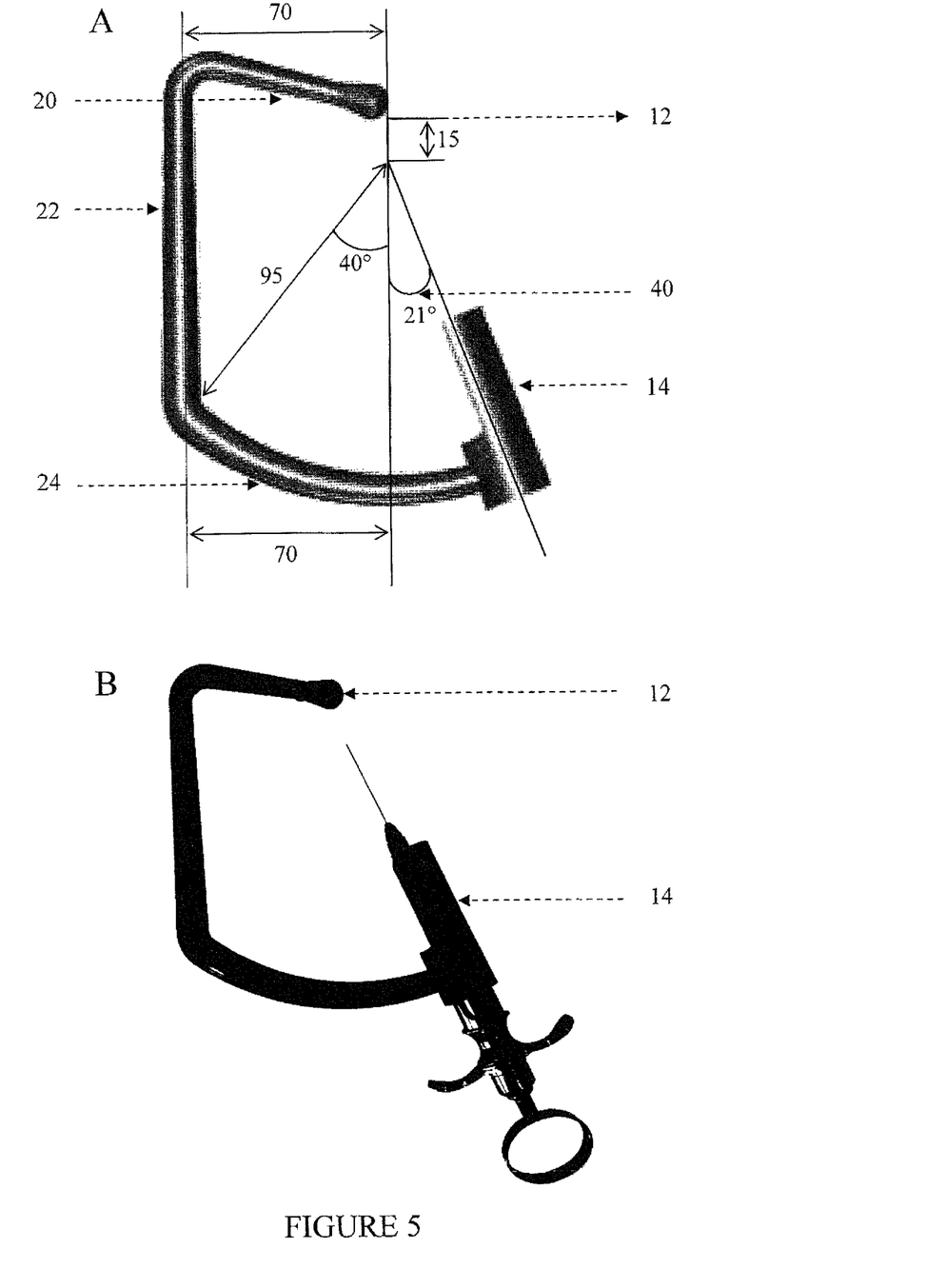
FIG. 5A shows a guiding device and FIG. 5B shows a guiding device having a syringe, according to another embodiment of the invention.

As shown in FIG. 5A, the orientation of guide tube 14 and retro-mandibular tip 12 are positioned such that the angle 40 is about 21°. Angle 40 is the angle between the axis of guide tube orientation and a straight axis (e.g., a straight axis parallel to second connecting arm 22 or a straight axis between the retromandibular tip 12 and a predetermined point in the connecting mechanism).

Guiding device 10 can be made of any suitable material, known to one of skilled in the art. Examples of such materials include, but are not limited to, polymers, plastics, thermoplastics, metals, alloys and combinations thereof. In a particular embodiment, guiding device 10 is made of a polymer.

Figure 6:
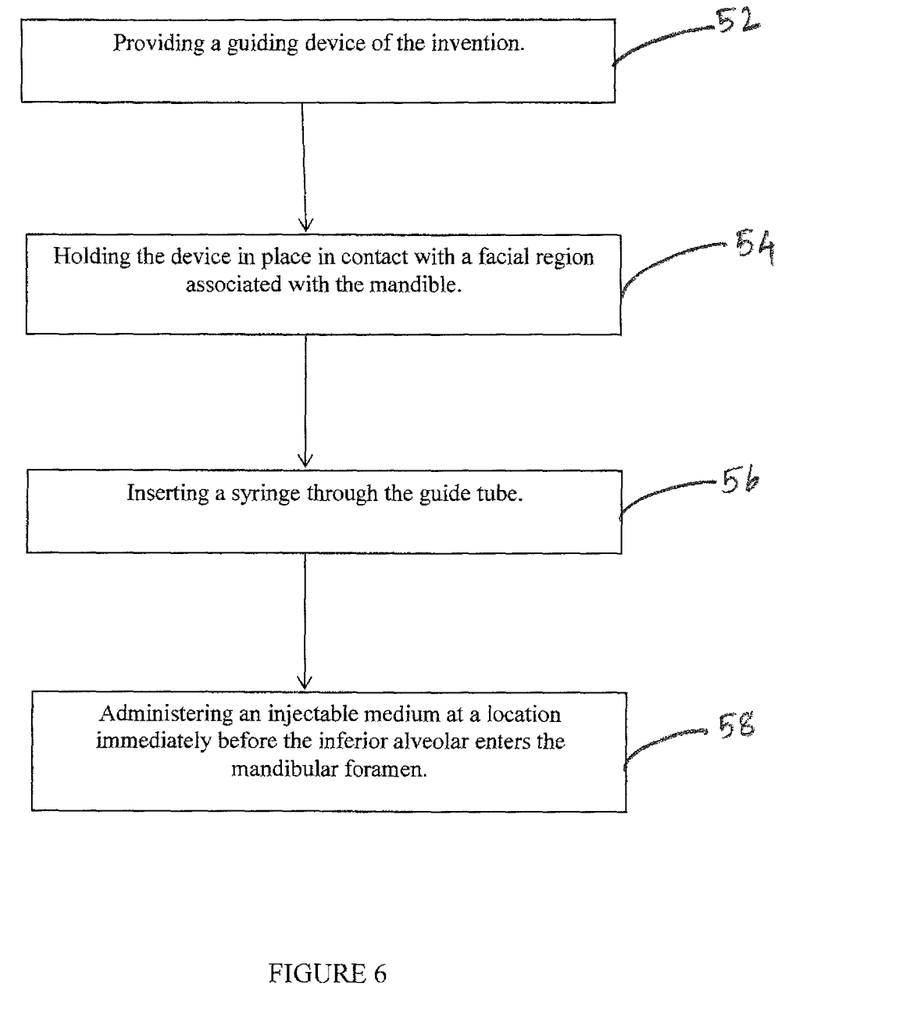
FIG. 6 shows a flow chart for administering an injection of anesthesia in the vicinity of an inferior alveolar nerve of a subject, according to another embodiment of the invention.

The invention also provides methods for administering an injection of anesthesia in the vicinity of an inferior alveolar nerve of a subject. As shown in FIG. 6, item 52, device 10 is provided. As shown in item 54, device 10 can be positioned in place in contact with a facial region relating to mandible 1. As shown in item 56, syringe 30 can be inserted through guide tube 14. The orientation of guide tube 14 and retro-mandibular tip 12 are positioned such that the guiding axis of the device 10 projects against medial surface 4 of the mandibular ramus 2 no more than the predetermined distance, discussed herein, from the posterior edge of the mandibular ramus 2. As shown in item 58, an injectable medium is administered at a location immediately before the inferior alveolar enters the mandibular foramen. Preferably, in administering an injection, standard accepted protocols may be utilized in conjunction with the nerve block guide of the present invention.

The guiding device 10 of the invention can also be used in conjunction with one or more complementary injection techniques, such as, for example, but not limited to, the Gow-Gates mandibular nerve block, Akinosi-Vazirani closed-mouth mandibular nerve block, intra-osseous anesthetic injection, periodontal ligament anesthetic injection, and retromolar technique.

The term "subject," as used herein, may refer to both human and non-human subjects.

Any patent or patent application publication cited herein is incorporated by reference herein in its entirety.

The following examples are presented in order to more fully illustrate the preferred embodiments of the invention. They should in no way be construed, however, as limiting the broad scope of the invention.

EXAMPLES

Example 1: Design of a Guiding Device for Inferior Alveolar Nerve Block

The availability of several techniques for inferior alveolar nerve analgesia in a targeted area of the pterygomandibular space reflects the difficulties faced by practitioners. The objective of this study was to design a guiding device for inferior alveolar nerve block. An analysis of 40 CT scans of facial masses aided in the determination of the most appropriate configuration of the guiding device. Depending on individual morphological characteristics, the projection point of the device was situated on the medial surface of the mandibular ramus, between 7.0 mm and 14.0 mm anterior to the posterior edge of the ramus.

Materials and Methods

Materials

The design of the device was conducted with CT scans made in the Medical Imaging Service at the Hospital of Troyes (France), on 40 consecutive patients aged 12 to 71 years (21 men, 19 women) with no exclusion criteria. These patients had undergone one of the following interventions: extraction of impacted third molars near the inferior alveolar nerve, treatment of impacted canines, pre-implant assessment, or excision of a cyst close to the inferior alveolar nerve.

The tomodensitometric sections were obtained with the aid of a Toshiba AQUILON 64 scanner (asu, Japan) with the following parameters: section thickness, 0.5 mm; pitch, 1.0 mm; and field size, 30.0 mm. The axial cuts studied (scale 1:1) were slices that passed the mandibular ramus, parallel to the inferior border of the body of the bone.

Method

For Inferior Alveolar Nerve Block (IANB) to be successful, the tip of the needle must be in contact with the medial surface of the mandibular ramus, above and behind the lingula of the mandible, which marks the anterior edge of the mandibular foramen. This site favors the diffusion of the solution toward the foramen.

Figure 7:
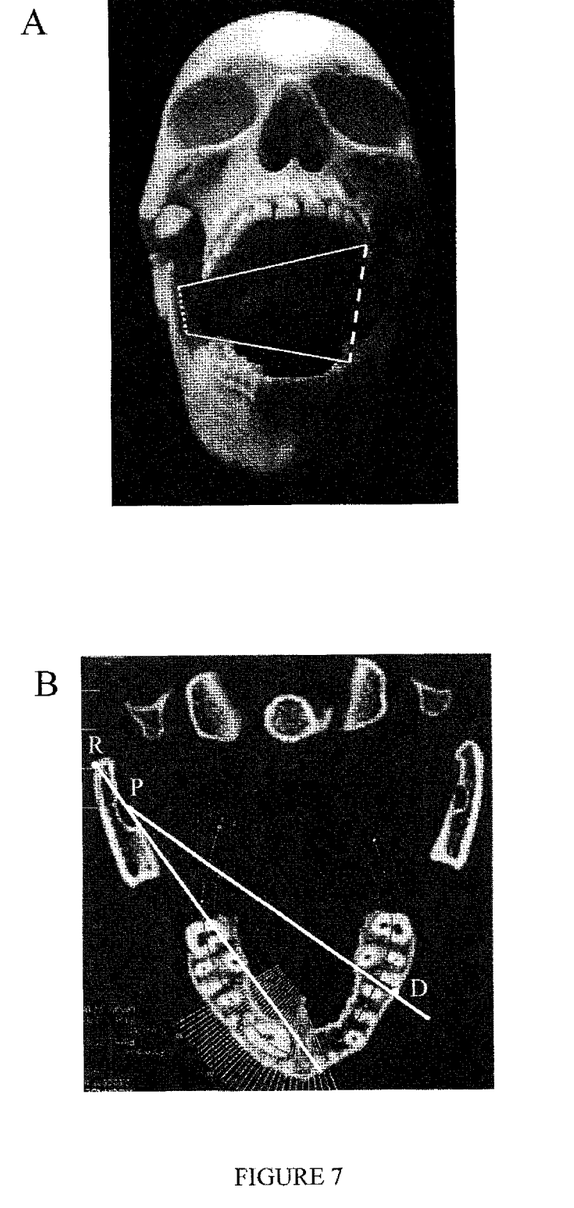
FIG. 7 shows projection plane and projection axis, according to another embodiment of the invention.

A projection plane precisely defined the orientation of the syringe at the moment of injection. This projection plane is passed by two axes (FIG. 7A).

The first axis was situated at the medial surface of the mandibular ramus, 14.0 mm anterior to its posterior edge. This axis was determined in such a way that it was always situated behind the lingula of the mandible and considered individual variations in the position of the lingula. Previously, it was reported that the position of the lingula can vary from one mandible to another by a distance of 14.0-23.0 mm anterior to the posterior edge of the mandibular ramus.

The second axis passed by the mesiobuccal cusp of the first mandibular molar opposite the side designated for analgesia, and by the contact point between the second premolar and the first maxillary molar opposite the side designated for analgesia. This axis was determined so that it would be situated sufficiently laterally in the oral cavity to avoid an anatomical obstacle: the temporal crest.

The orientation of the body of the syringe in the projection plane and according to the highest axis in the oral cavity is compatible with successful analgesia. Because the projection plane cannot be visualized in the mouth, this study was undertaken with axial CT sections.

The projection angle between the projection plane and the sagittal plane passing by the posterior edge of the mandibular ramus varies among individuals and depends on the shape of the dental arches and the orientation of the mandibular ramus. To evaluate the amount of variation in this projection angle, the inventor selected three reference points on each tomodensitometric section (FIG. 7B): (1) the retro-mandibular point R, situated on the posterior-lateral angle of the mandibular ramus, at the junction of the posterior edge and the lateral surface of the mandibular ramus on the side designated for analgesia; (2) the projection point P, situated on the medial surface of the mandibular ramus, 14.0 mm anterior to point R; and (3) the dental point D, situated for axial sections passing by the maxillary teeth on the contact point between the second premolar and the first maxillary molar, opposite the side designated for analgesia. For axial sections passing by the mandibular teeth, point D was situated on the mesio-vestibular cusp of the first molar opposite the side designated for analgesia.

Two axes corresponded to these three points, the ramus axis (R, P) and the projection axis (P, D). These axes formed two respective angles with the sagittal plane passing by point R: the ramus angle and the projection angle, which inspired the design of the guiding device.

As shown in FIG. 7A, the projection plane passed by two axes: the axis situated at the medial surface of the mandibular ramus, 14.0 mm anterior to its posterior edge (line in pointillets), and the axis passed by the mesiobuccal cusp of the first mandibular molar opposite the side designated for analgesia, and by the contact point between the second premolar and the first maxillary molar opposite the side designated for analgesia (dashed line).

As shown in FIG. 7B, two axes, the ramus axis (R, P) and the projection axis (P, D) corresponded to three points: the retro-mandibular point R, situated on the posterior-lateral angle of the mandibular ramus, the projection point P, situated on the medial surface of the mandibular ramus, 14.0 mm anterior to point R; and the dental point D, situated on the contact point between the second premolar and the first maxillary molar, opposite the side designated for analgesia.

Results

Analysis of Tomodensitometric Sections

The results of the CT scans are presented in Table 1 below.

TABLE 1

Angles Measured in the 40 CT sections analyzed.

| Patient | Age | Gender | Reason for Exam | Ramus Angle | Projection Angle |
|---|---|---|---|---|---|
| 1 | 12 y | F | Impacted canine | 37° | 53° |
| 2 | 59 y | M | Implant | 22° | 53° |
| 3 | 42 y | M | Cyst | 31° | 53° |
| 4 | 17 y | M | Impacted canine | 35° | 53° |
| 5 | 41 y | F | Implant | 36° | 54° |
| 6 | 25 y | F | Cyst | 26° | 55° |
| 7 | 14 y | M | Impacted canine | 26° | 55° |
| 8 | 14 y | M | Impacted canine | 22° | 55° |
| 9 | 14 y | M | Impacted canine | 37° | 55° |
| 10 | 36 y | F | Implant | 31° | 55° |
| 11 | 38 y | M | Implant | 35° | 56° |
| 12 | 41 y | F | Implants | 42° | 56° |
| 13 | 13 y | F | Impacted canine | 36° | 56° |
| 14 | 56 y | F | Implant | 28° | 57° |
| 15 | 46 y | F | Third molar | 42° | 57° |
| 16 | 57 y | F | Cyst | 30° | 57° |
| 17 | 59 y | M | Implant | 28° | 58° |
| 18 | 12 y | F | Impacted canine | 36° | 58° |
| 19 | 42 y | F | Implant | 31° | 58° |
| 20 | 38 y | F | Implant | 35° | 60° |
| 21 | 59 y | M | Implant | 29° | 60° |
| 22 | 55 y | F | Implant | 35° | 61° |
| 23 | 14 y | F | Impacted canine | 28° | 62° |
| 24 | 65 y | M | Implants | 33° | 58° |
| 25 | 17 y | M | Impacted canine | 26° | 55° |
| 26 | 54 y | M | Implants | 26° | 59° |
| 27 | 22 y | M | Third molar | 36° | 57° |
| 28 | 61 y | M | Implants | 26° | 53° |
| 29 | 28 y | M | Implants | 32° | 53° |
| 30 | 17 y | M | Impacted canine | 36° | 56° |
| 31 | 64 y | M | Implant | 29° | 54° |
| 32 | 39 y | M | Implants | 32° | 53° |
| 33 | 13 y | F | Impacted canine | 34° | 61° |
| 34 | 13 y | F | Impacted canine | 38° | 60° |
| 35 | 37 y | F | Third molar | 26° | 55° |
| 36 | 71 y | M | Implant | 40° | 59° |
| 37 | 39 y | M | Implant | 32° | 56° |
| 38 | 71 y | M | Implants | 38° | 54° |
| 39 | 40 y | F | Implant | 27° | 55° |
| 40 | 65 y | F | Implant | 31° | 56° |

*Maximum and minimum values in bold.

The projection angle varied from 53° to 62°, with an average of 56°. The ramus angle varied from 22° to 42°, with an average of 32°.

Taking into account the variability among individuals, the inventor of the instant application configured the device so that its guiding axis would project against the medial surface of the mandibular ramus no more than 14.0 mm anterior to the posterior edge of the mandibular ramus for all patients (that is, always behind the mandibular foramen).

It was possible to record the orientation of the projection axis in relation to point R chosen on one of the tomodensitometric sections on the guiding device, such that the point of projection indicated by the device would contact bone 14.0 mm anterior to the posterior edge of the mandibular ramus. Because the projection angle varies among individuals, it was necessary to verify whether the position of the projection point indicated by the device is compatible with analgesia by superimposing the device at points R and D of other tomodensitometric sections. For this reason, sections from patients presenting the most extreme projection angles were analyzed, that from patient 1 presented the most closed projection angle (FIG. 8A), whereas that from patient 23 presented the most open projection angle (FIG. 8B).

When the orientation of the projection axis in relation to point R in patient 23 was recorded, and this point and the axis were superimposed on points R and D, respectively, in patient 1, the projection point P' indicated by the device was in bone contact 24.0 mm anterior to point R (FIG. 8C). This position of the projection point anterior to the lingula of the mandible does not favor the diffusion of the solution toward the foramen and does not allow the infiltration of the inferior alveolar nerve.

Conversely, when the orientation of the projection axis in relation to point R in patient 1 was recorded and this point and this axis were superimposed on points R and D, respectively, in patient 23, the projection point P''' indicated by the device was in bone contact 7.0 mm anterior to point R (FIG. 8D). This would be behind the lingula of the mandible, favorable site for the diffusion of the solution toward the foramen.

Thus, the position of point R in relation to the projection axis established for patient 1 was used to configure the device, such that the projection axis protruded onto the medial surface of the mandibular ramus for all patients, at a distance of 7.0-14.0 mm anterior to the posterior edge of the mandibular ramus.

Figure 8:
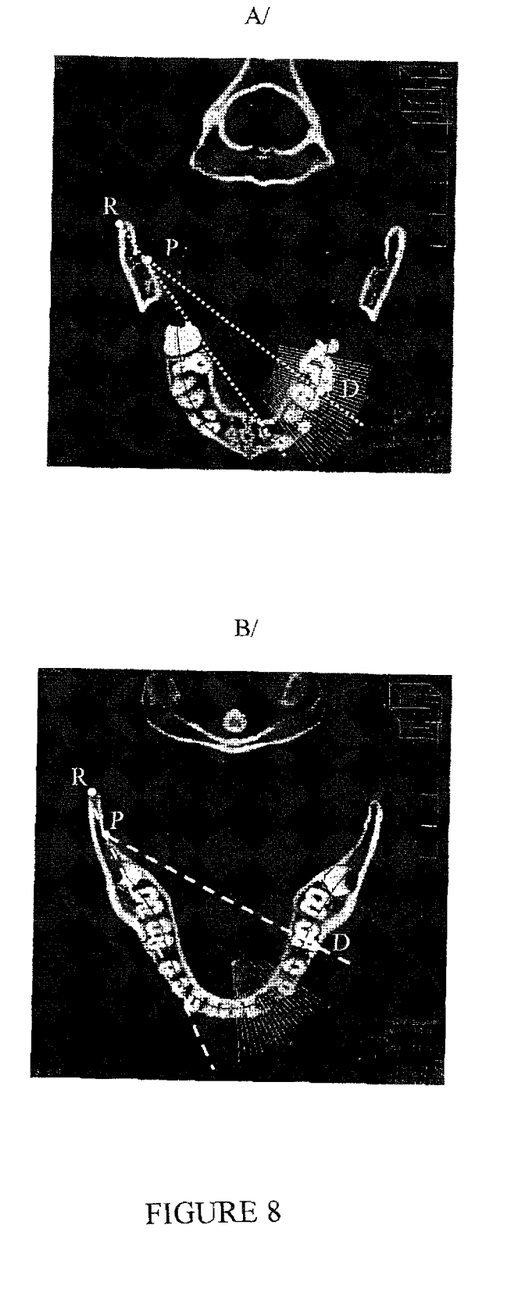
FIG. 8 shows CT scans with the projection angles, according to another embodiment of the invention.

CT scans with the projection angles are shown in FIG. 8. FIG. 8A shows CT section from patient 1, presenting the most closed projection angle, 53°. The ramus axis (R, P) and the projection axis (P, D) are represented by line in pointillet. FIG. 8B shows CT section from patient 23, presenting the most open projection angle, 62°. The ramus axis (R, P) and the projection axis (P, D) are represented by dashed lines.

FIG. 8C shows recording of the orientation of the projection axis in relation to point R in patient 23 (dashed line) and superimposition of this point and this axis, respectively, on points R and D of the CT section from patient 1. The projection point P' indicated by the device is situated on bone, 24.0 mm anterior to point R. FIG. 8D shows recording of the orientation of the projection axis in relation to point R in patient 1 (line in pointillet) and superimposition of this point and this axis, respectively, on points R and D of the CT section from patient 23. The projection point P''' indicated by the device is situated on bone, 7.0 mm anterior to point R.

As shown in FIG. 5A, the guiding device 10 of the invention includes a retro-mandibular tip 12 and a guide tube 14 connected to each other by three junction arms 20, 22, and 24. The position of the retro-mandibular tip 12 and the orientation of the guide tube 14 were configured according to the characteristics of patient 1, such that the outermost point of the retro-mandibular tip 12 and the axis of the guide tube 14 would coincide, respectively, with point R and with the projection axis established on the tomodensitometric section from patient 1. FIG. 5A shows that the anterior-internal angle of the retro-mandibular tip 12 is identical to that of point R, and the axis of the guide tube 14 is the same as the axis of projection located on the CT section from patient 1.

As shown in FIG. 5B, the internal diameter of the guide tube 14 corresponded to that of the body 32 of the syringe 30, which could therefore slide freely along the guide tube 14, following the same axis.

The causes of failure of anesthesia in current practice are varied. These causes may be due to a lack of knowledge of anatomical structures or to a lack of experience of the practitioner. One of the advantages of the device 10 of the invention described herein is to indicate the axis at which the needle must be applied to put its tip in contact with the bone above and posterior to the lingula. The device 10 applied against the occlusal surfaces of the maxillary teeth improves the practitioner's gestural precision by stabilizing the point of needle penetration. The device 10 of the invention can inject an analgesic solution above and behind the mandibular foramen in a reliable and reproducible manner.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A device for administering an injection in the vicinity of an inferior alveolar nerve, in a subject having a mandible, a mandibular foramen, and a mandibular ramus, the device comprising:
   a retro-mandibular tip;
   a guide tube adapted to receive a syringe having a needle; and
   a connecting mechanism having a first, a second and a third connecting arm, said first connecting arm comprising a first end of the connecting mechanism fixedly connected to the retro-mandibular tip, the first end operably linking said retro-mandibular tip to said second connecting arm, said second connecting arm operably linking said first connecting arm to said third connecting arm, and said third connecting arm operably linking said second connecting arm to said guide tube at a second end of the connecting mechanism, the connecting mechanism connecting the retro-mandibular tip, arranged at the first end, to the guide tube, the guide tube being fixedly attached to the connecting mechanism at the second end of the connecting mechanism,
   wherein said guide tube comprises a fixed position mechanical stop dimensioned and arranged in an interior of the guide tube so as to stop advancement of said syringe as the syringe passes through said guide tube, at a point at which the syringe needle is located at a predetermined distance from a posterior edge of the subject's mandibular ramus, such that the retro-mandibular tip is maintained at a fixed, non-movable position and at a fixed distance with respect to the mechanical stop;
   wherein during injection, said retro-mandibular tip of said device is positioned so as to contact a facial region associated with the subject's mandible, and
   wherein the device is configured such that the predetermined distance and an angle between an axis of the guide tube orientation and a straight axis parallel to said second connecting arm are such that once the syringe has been received in the guide tube, no operator adjustment is required, in performing the injection, regarding either a syringe angle or a needle depth.

2. The device of claim 1, wherein said mechanical stop is adapted to stop the advancement of said syringe when the syringe needle is located at a distance, ranging between about 7 mm and about 25 mm, from the posterior edge of the subject's mandibular ramus.

3. The device of claim 1, wherein said mechanical stop is adapted to stop the advancement of said syringe when the syringe needle is located at a distance, ranging between about 7 mm and about 14 mm, from the posterior edge of the subject's mandibular ramus.

4. The device of claim 1, wherein said mechanical stop is adapted to stop the advancement of said syringe when the syringe needle is located at a distance of about 15 mm from the posterior edge of the subject's mandibular ramus.

5. The device of claim 1, wherein said guide tube comprises an inlet port and an outlet port and wherein the mechanical stop is adapted to stop the advancement of said syringe such that the distance between an edge of the inlet port and a retro-mandibular tip edge (ER) equals the sum of the distance between the edge of the inlet port and a point of the needle (EP) and the distance between the point of the needle and the retro-mandibular tip edge (PR).

6. The device of claim 5, wherein the mechanical stop is adapted to stop the advancement of said syringe, in accordance with the following relationship:

$$ER=EP+PR,$$

wherein ER refers to the distance between the edge of the inlet port and the retro-mandibular tip edge, EP refers to the distance between the edge of the inlet port and the point of the needle, and PR refers to the distance between the point of the needle and the retro-mandibular tip edge.

7. The device of claim 5, wherein the position of said guide tube also reflects a length of the needle (PF) and a length of a portion of a syringe body (FC).

8. The device of claim 5, wherein the outlet port of said guide tube has a reduced diameter relative to the diameter of the inlet port such that the guide tube abuts against the end of a syringe body.

9. The device of claim 1, wherein said guide tube comprises an inlet port and an outlet port and wherein the mechanical stop is adapted to stop the advancement of said syringe such that the distance between an edge of the outlet port and a retro-mandibular tip edge (SR) equals the sum of a needle length (PF) and the distance between a point of the needle and the retro-mandibular tip edge (PR).

10. The device of claim 9, wherein the mechanical stop is adapted to stop the advancement of said syringe, in accordance with the following relationship:

$$SR=PF+PR,$$

wherein SR refers to the distance between the edge of the outlet port and the retro-mandibular tip edge, PF refers to the needle length, and PR refers to the distance between the point of the needle and the retro-mandibular tip edge, and wherein said PR ranges from about 7 mm to about 25 mm.

11. The device of claim 1, wherein the orientation of the guide tube and retro-mandibular tip are positioned such that an angle between an axis of the guide tube orientation and a straight axis parallel to said second connecting arm is about 21°.

12. The device of claim 1, wherein said device is made of material selected from the group consisting of polymers, plastics, thermoplastics, metals, alloys and combinations thereof.

13. The device of claim 1, wherein said device comprises polymer.

14. The device of claim 1, wherein said subject is a human subject.

15. A method of administering an injection in the vicinity of an inferior alveolar nerve of a subject, the method comprising the steps of:
   a) providing the device of claim 1;
   b) holding said device in place in contact with the facial region associated with the subject's mandible;
   c) inserting the syringe through said guide tube; and
   d) administering an injectable medium at a location immediately before the inferior alveolar nerve enters the subject's mandibular foramen.

16. A method of administering an injection in the vicinity of an inferior alveolar nerve of a subject, the method comprising the steps of:
   a) providing the device of claim 14;
   b) holding said device in place in contact with the facial region associated with the subject's mandible;
   c) inserting the syringe through said guide tube; and
   d) administering an injectable medium at a location immediately before the inferior alveolar nerve enters the subject's mandibular foramen.

17. A guiding device for administering an injection in the vicinity of an inferior alveolar nerve, in a subject having a mandible, a mandibular foramen, and a mandibular ramus, the device comprising:
   a retro-mandibular tip;
   a guide tube adapted to receive a syringe having a needle; and
   a connecting mechanism having a first, a second and a third connecting arm, said first connecting arm comprising a first end of the connecting mechanism fixedly connected to the retro-mandibular tip, the first end operably linking said retro-mandibular tip to said second connecting arm, said second connecting arm operably linking said first connecting arm to said third connecting arm, and said third connecting arm operably linking said second connecting arm to said guide tube at a second end of the connecting mechanism, the connecting mechanism connecting the retro-mandibular tip, arranged at the first end, to the guide tube, the guide tube being fixedly attached to the connecting mechanism at the second end of the connecting mechanism,
   wherein said guide tube comprises a fixed position mechanical stop dimensioned and arranged in an interior of the guide tube so as to hold said syringe such that the syringe needle is located at a distance, ranging between about 7 mm and about 25 mm, from a posterior edge of the subject's mandibular ramus, such that the retro-mandibular tip is maintained at a fixed, non-movable position and at a fixed distance with respect to the mechanical stop;
   wherein during injection, said retro-mandibular tip of said guiding device is positioned so as to contact a facial region associated with the subject's mandible, and
   wherein the device is configured such that the distance from the posterior edge of the subject's mandibular ramus, and an angle between an axis of the guide tube orientation and a straight axis parallel to said second connecting arm are such that once the syringe has been received in the guide tube, no operator adjustment is required, in performing the injection, regarding either a syringe angle or a needle depth.

18. A device for administering an injection in the vicinity of an inferior alveolar nerve, in a subject having a mandible, a mandibular foramen, and a mandibular ramus, the device comprising:
    a retro-mandibular tip;
    a guide tube adapted to receive a syringe having a needle; and
    a connecting mechanism having a first, a second and a third connecting arm, said first connecting arm comprising a first end of the connecting mechanism fixedly connected to the retro-mandibular tip, the first end operably linking said retro-mandibular tip to said second connecting arm, said second connecting arm operably linking said first connecting arm to said third connecting arm, and said third connecting arm operably linking said second connecting arm to said guide tube at a second end of the connecting mechanism, the connecting mechanism connecting the retro-mandibular tip, arranged at the first end, to the guide tube, the guide tube being fixedly attached to the connecting mechanism at the second end of the connecting mechanism,
    wherein said guide tube comprises a fixed position mechanical stop dimensioned and arranged in an interior of the guide tube so as to stop advancement of said syringe as the syringe passes through said guide tube, at a predetermined point in said syringe,
    wherein said mechanical stop is adapted to stop the advancement of said syringe when the syringe needle is located at a distance, ranging between about 7 mm and about 25 mm, from a posterior edge of the subject's mandibular ramus, such that the retro-mandibular tip is maintained at a fixed, non-movable position and at a fixed distance with respect to the mechanical stop;
    wherein during injection, said retro-mandibular tip of said device is positioned so as to contact a facial region associated with the subject's mandible, and
    wherein the device is configured such that the distance from the posterior edge of the subject's mandibular ramus, and an angle between an axis of the guide tube orientation and a straight axis parallel to said second connecting arm are such that once the syringe has been received in the guide tube, no operator adjustment is required, in performing the injection, regarding either a syringe angle or a needle depth.

* * * * *